US00PP31145P3

(12) United States Plant Patent
Brown et al.

(10) Patent No.: US PP31,145 P3
(45) Date of Patent: Dec. 3, 2019

(54) APPLE TREE NAMED 'NY 109'

(50) Latin Name: ***Malus* x *domestica***
Varietal Denomination: NY 109

(71) Applicant: Cornell University, Ithaca, NY (US)

(72) Inventors: Susan Brown, Geneva, NY (US); Kevin Maloney, Phelps, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/932,641

(22) Filed: Mar. 30, 2018

(65) Prior Publication Data

US 2019/0307035 P1 Oct. 3, 2019

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./161
See application file for complete search history.

*Primary Examiner* — Susan McCormick Ewoldt
(74) *Attorney, Agent, or Firm* — Pepper Hamilton LLP

(57) ABSTRACT

This invention relates to a new and distinctive variety of a *Malus* x *domestica* apple tree named 'NY109', particularly characterized by its overall superior horticultural performance and consistency, including excellent fruit quality at harvest by having firm, juicy, high sugar and high acid and flavorful fruit with great potential for marketing as both a fresh apple and as value-added processed apple products, such as for hard and sweet cider and for baking, is disclosed.

7 Drawing Sheets

FIELD OF THE INVENTION

The present invention relates to a new and distinct variety of apple tree designated as 'NY 109'. The plant is botanically known as *Malus* x *domestica*.

BACKGROUND OF THE INVENTION

Apples are an economically important crop internationally. There is an ongoing need to develop new varieties of apple trees with improved characteristics to meet the changing needs of the producer, processor, and consumer.

BRIEF SUMMARY OF THE INVENTION

The following traits define the new plant as a unique plant, distinguishing it from other commercial varieties in the region.

This invention is directed to an improved variety of apple tree. In particular, the invention relates to a new and distinct variety of apple tree (*Malus* x *domestica*), which has been denominated as 'NY 109'. The new variety 'NY109' has excellent flavor, with a good balance of sweetness and acidity and good aromatics. The fruit are firm, medium size, and unique in appearance with a light red blush color, yellow background color, and fine russeting of the fruit finish giving 'NY109' an antique or heirloom-like appearance. The fruit have multiple uses. The fruit can be used for fresh consumption, in processing, and in sweet and hard cider production.

'NY109' was selected for its high flavor, robust aromatics, and overall horticultural performance and consistency, and good balance of high sugar and high acidity of the fruit.

Apple tree 'NY109' is a hybrid that originated from a planned controlled cross in 1997 in Geneva, N.Y. The seed parent (female parent) is *Malus* x *domestica* Golden Glory™ apple tree 'DS-165' (U.S. Plant Pat. No. 7,851). Golden Glory is a semi-spur limb mutation of Smoothie® Golden Delicious a limb mutation of the popular cultivar 'Golden Delicious'. The pollen parent (male parent) is *Malus* x *domestica* 'NY752' apple tree (unpatented). This is a proprietary advanced breeding selection at Cornell. 'NY 752' is a hybrid of 'Starkspur Golden Delicious' x NY88 ('Monroe' x 'Melrose').

The original cross, designated '729', was made by applying pollen from a 'NY752' apple tree onto emasculated flowers of a Golden Glory™ apple tree in Geneva, N.Y. in 1997. Seedlings were planted on their own roots in an orchard in Geneva, N.Y. in 1999, after being stratified and grown in the greenhouse. One seedling, designated NY97729-109, was selected from a field population of 485 seedlings on the basis of excellent fruit quality, firm flesh, and unique and attractive fruits. Additional trees of seedling NY97729-109 were produced by clonal propagation starting in 2004 and in subsequent years in Geneva, N.Y. These additional trees were evaluated for fruit and tree characteristics, pest resistance, and trueness-to-type. NY97729-109 was later designated as 'NY109'.

'NY109' was first asexually (clonally) propagated by chip budding onto apple tree rootstock 'M.9' (unpatented) in 2004 in a research nursery in Geneva, N.Y. Subsequent asexual reproduction of 'NY109' has been successful using traditional grafting and budding methods of propagation, demonstrating that the unique combination of traits of the asexually propagated trees is identical in all appearances to the original tree. Asexual reproduction of this new variety by grafting and budding onto rootstocks shows that the characteristics of asexually propagated trees are true-to-type and are established and transmitted through succeeding propagations.

Distinguishing Characteristics of 'NY109'

Seed Parent: Golden Glory™. The seed parent *Malus* x *domestica* Golden Glory™ is an apple variety known for its superior fruit quality, characterized by having fruit with solid yellow color, and a firm and juicy fruit texture with smooth skin. When compared to Golden Glory™, 'NY109' has similar scion vigor and tree characteristics. 'NY109' has similar fruit quality characteristics to Golden Glory™ in its firm texture and medium fruit size, however 'NY109' produces fruit that have a red blush color compared to the solid yellow color of Golden Glory™. 'NY109' is different from the commercial variety 'New York 2' (RubyFrost®, U.S. Plant Pat. No. 22,207) in having conic fruit shape compared to the globose fruit shape in 'New York 2'. 'NY109' is different in fruit appearance from 'New York 2' having more skin russet and a lighter fruit color compared to the mostly full darker red color of 'New York 2'. 'NY109' has more intense flavor compared to 'New York 2', having higher brix and acidity levels.

Pollen Parent: NY 752. The pollen parent 'NY 752' is an advanced breeding selection from the Cornell program. When compared to 'NY109', the pollen parent 'NY 752' produces fruit that are slightly larger and have a broader shape.

BRIEF DESCRIPTIONS OF THE DRAWINGS

The accompanying images illustrate characteristics of 'NY109'. The colors shown are as true as can be obtained reasonably by conventional photographic procedures. However, the colors in the images may vary with lighting conditions and, therefore, color characteristics of this new variety should be determined with reference to the observations described herein, rather than from the photographs alone. The photographs are from trees that are 5-years-old for FIG. 1, and from trees that are 10-years-old for FIG. 2 to FIG. 7.

Figure 1:
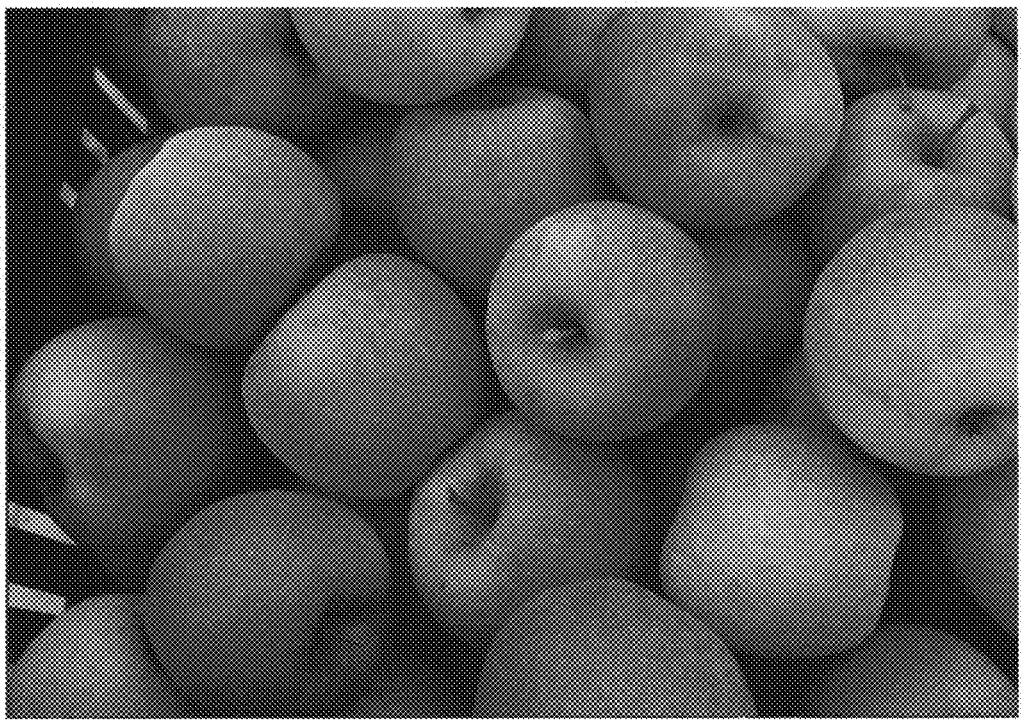
FIG. 1 is a color photograph depicting a bushel of fruit of apple tree variety 'NY109', depicting the range in fruit coloring and the typical fruit size and shape.
Figure 2:
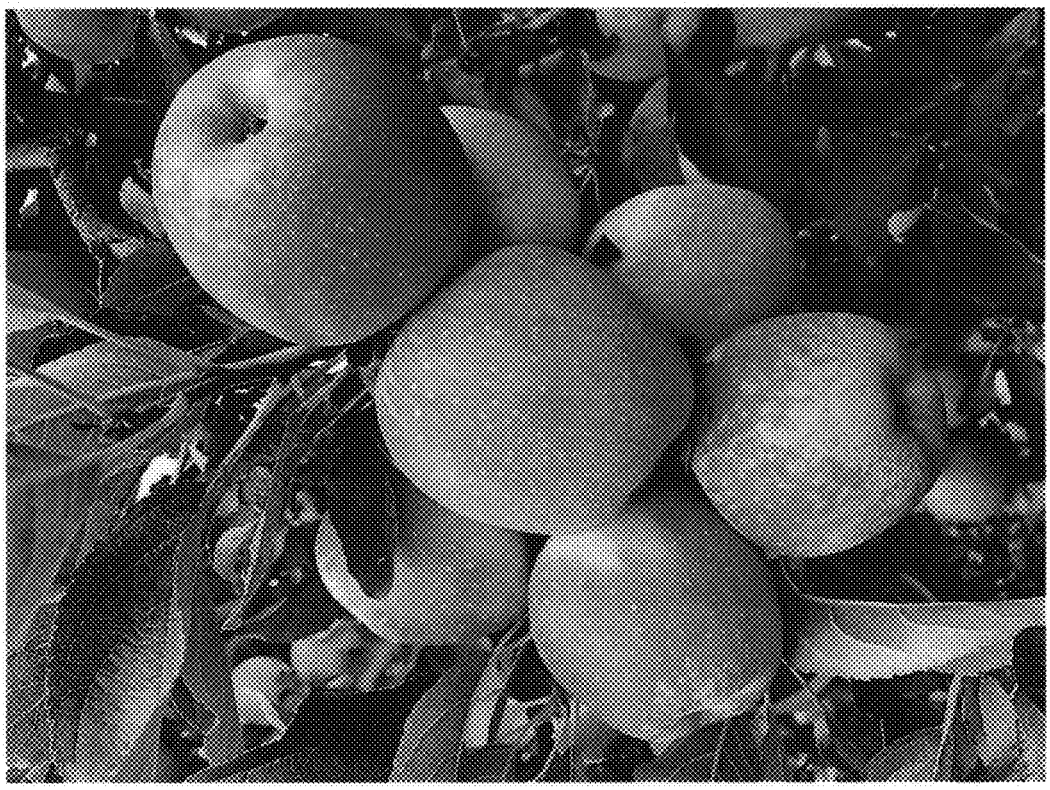
FIG. 2 is a color photograph depicting a close up of fruit of apple tree variety 'NY109' at harvest.
Figure 3:
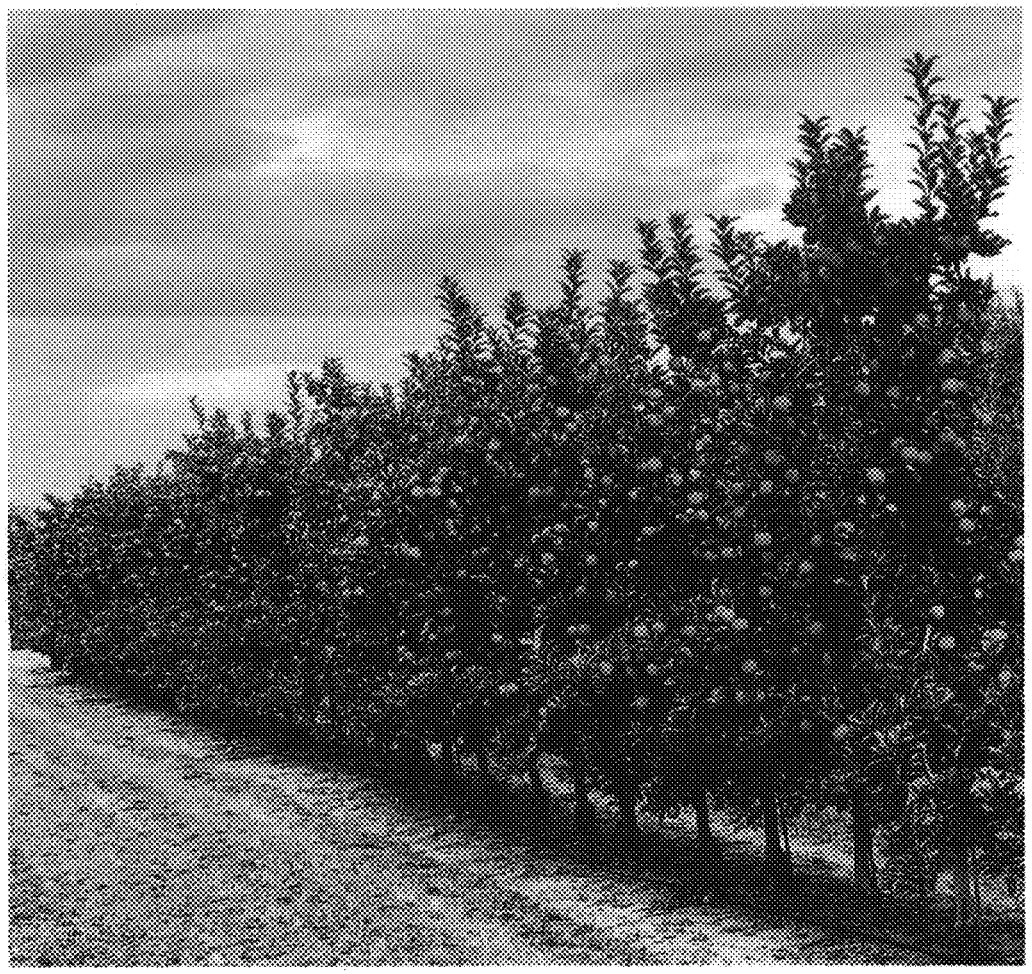
FIG. 3 is a color photograph depicting a row of trees of apple tree variety 'NY109' in orchard.
Figure 4:
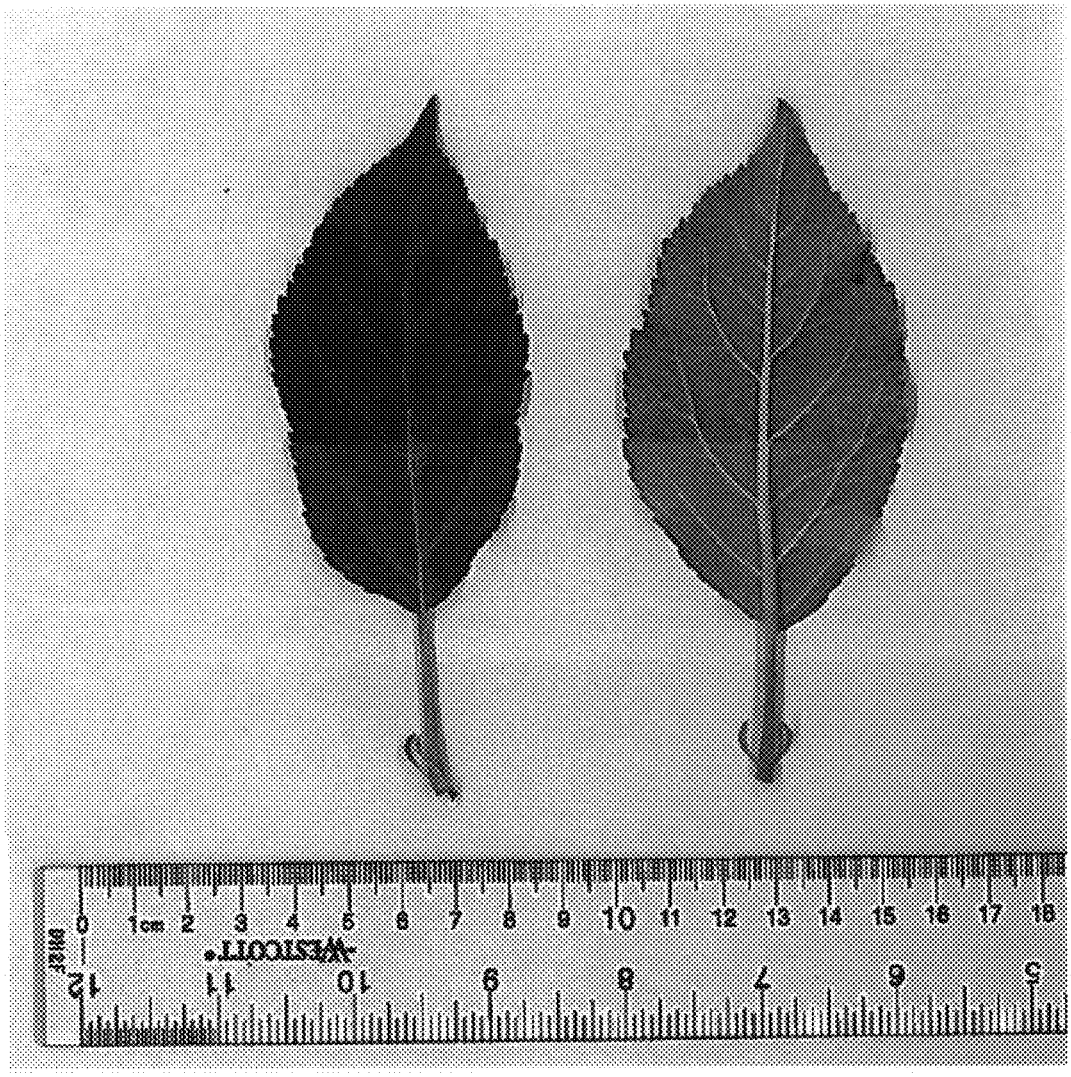
FIG. 4 is a color photograph depicting both an upper and lower surface of a mature leaf of apple tree variety 'NY109'.
Figure 5:
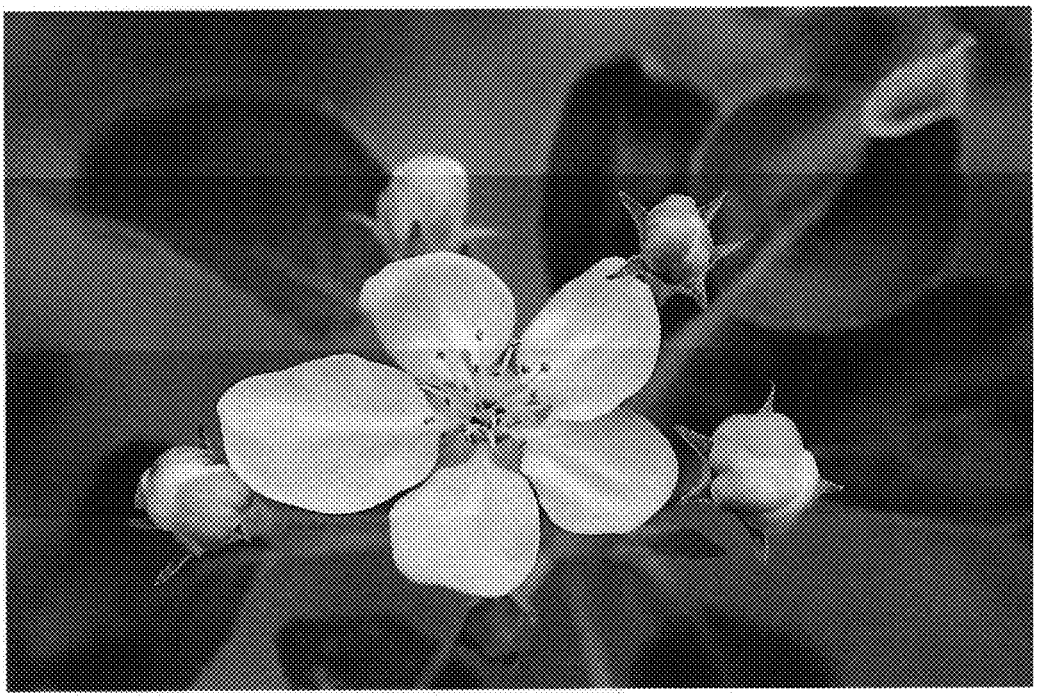
FIG. 5 is a color photograph depicting a flower cluster of apple tree variety 'NY109'.
Figure 6:
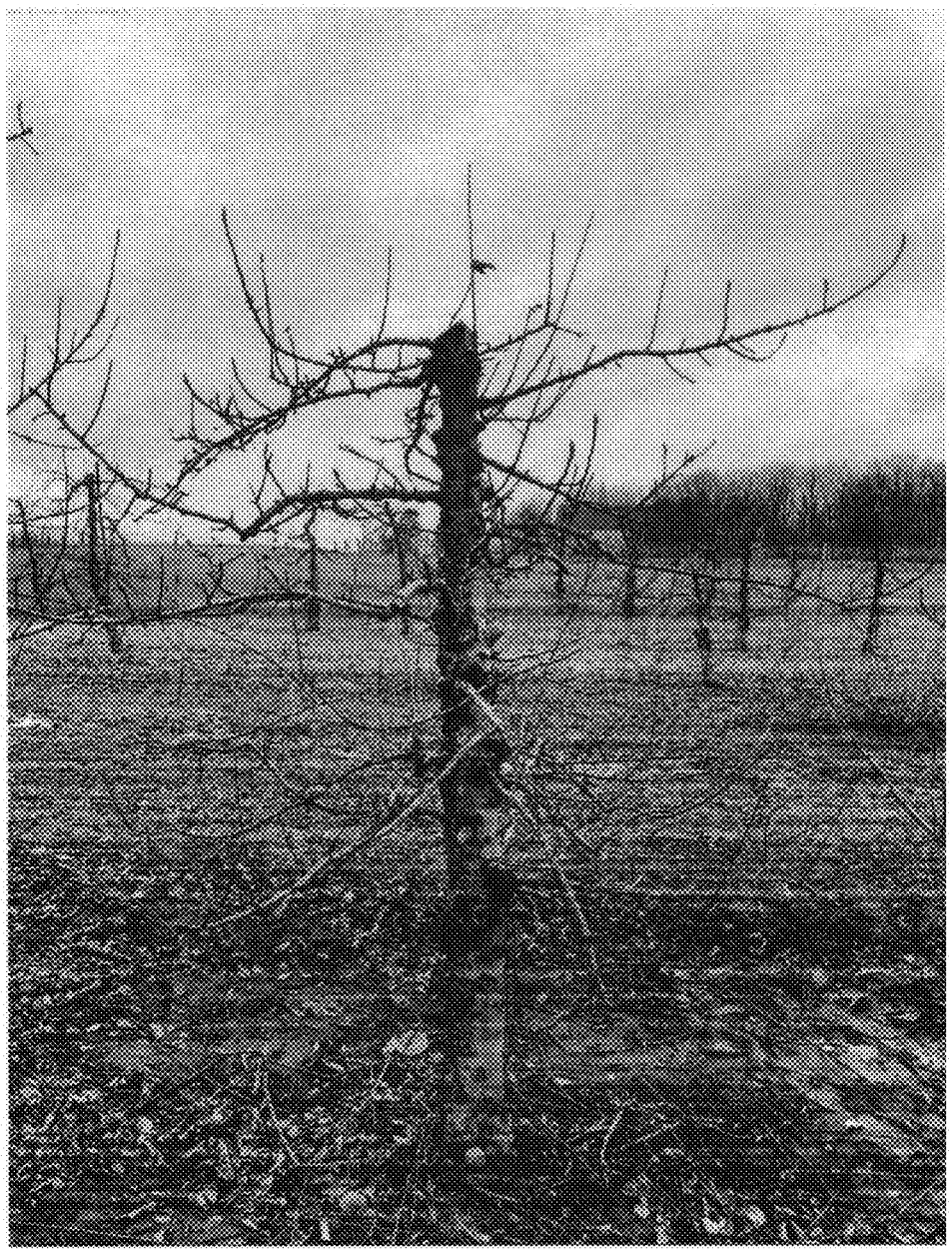
FIG. 6 is a color photograph depicting the original, dormant, free-standing seedling tree of apple tree variety 'NY109'.
Figure 7:
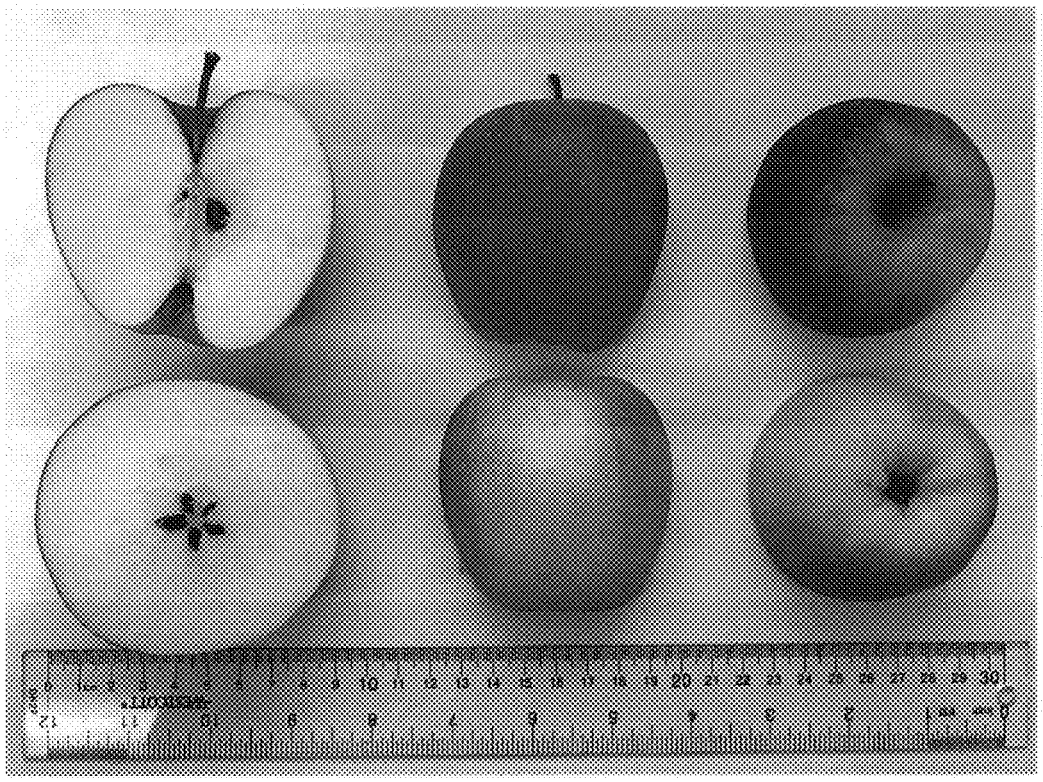

FIG. 7 is a color photograph depicting six views of a typical fruit of apple tree variety 'NY109'. The fruit at the top left depicts a cross section of 'NY109' fruit cut longitudinally from top to bottom. The fruit at the top middle depicts a side view of the sun-exposed side of 'NY109' fruit. The fruit at the top right depicts a stem and stem cavity of 'NY109' fruit. The fruit at the bottom left depicts a cross section of 'NY109' fruit cut horizontally through the seed cavity. The fruit at the bottom middle depicts a side view of the shaded side of 'NY109' fruit. The fruit at the bottom right depicts a calyx and basin area of 'NY109' fruit.

DETAILED BOTANICAL DESCRIPTION

The following description sets forth the distinctive characteristics of apple tree 'NY109'. The following description is based on the originally identified apple tree and asexually reproduced progeny grown in Geneva, N.Y., which is in USDA Plant Hardiness Zone 6A.

Referring more specifically to the details of the new and distinct apple tree variety 'NY109', unless otherwise stated, the following observations and characteristics have been taken since 1999 from a number of trees in different orchards to provide consistent descriptions.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society Colour Chart (R.H.S.C.C.), copyright 2001.

Tree: Medium in size; standard upright habit; medium vigor; early bearing on spurs. Twelve-year-old managed trees have an average height of 3.7 m, spread of 2.0 m, and average trunk diameter of 7.0 cm at 30 cm above soil line. Trees are conducive to both free standing and trellis-supported production systems. Approximate bud burst is around April 15 in Geneva, N.Y.

Tree trunk: One-year-old dormant wood surface color is RHSCC Brown group 200B. Four-year-old dormant wood surface color is Brown group RHSCC N200B. Bark lenticels are medium, round to elongate in shape, average 4 per square centimeter, and range from 0.5 mm to 6.8 mm in length.

Branch: Branch diameter of four-year-old wood is 21.7 mm. Branch angle is flat, typically 10 degrees to 40 degrees above the horizontal.

Leaf: Leaves are medium in size. Alternate in arrangement. Average leaf blade length is 103 mm and average blade width is 56 mm. Basal shape is rounded, apex is convex. Upper surface is smooth, very fine pubescence on lower surface. Concave-convex in cross section; upward in pose; medium glossiness of upward (adaxial) side; serrate margin indentation; average 2.2 serrations per centimeter. The color of the upper leaf blade surface is most similar to RHSCC 139A (Green) and the color of upper veins is RHSCC 191B (Greyed-green). The color of lower leaf blade surface is RHS 138D (Green) and the color of lower veins is RHSCC 191C (Greyed-green). Leaf petioles are medium in length, with an average length of 29 mm and diameter of 2.6 mm. The colors of petiole are RHSCC 191B (Greyed-green), 138B (Green), 195B (Greyed-green) and the color of the tinged petiole base is RHSCC 182B (Greyed-red). Stipules average 10.6 mm in length and 2.3 mm in width.

Flower: Flower color at the "pink" phenology stage is RHSCC Red-purple group 63C. Flower petals do not overlap in open flowers, mostly meeting or have a slight space between them. Flower cluster width averages 36 mm. There are five petals per flower and petals are mostly flat and slightly cupped upward. Both upper and lower surfaces are smooth. Average petal length is 17 mm, and average petal width is 12 mm. Flower petal color when open is white (RHSCC White group N155C), with some petal veins having a pink tinge of RHSCC Red-purple group 63D. Flowers are self sterile and require pollination by another diploid apple of the same bloom period. Approximate bloom time May 7 and duration 6 days in Geneva, N.Y.

Flower pedicel color: RHSCC Yellow-green 148B. Length 30 mm, width 1.2 mm.

Stamens: 20 stamens per flower, average 8.7 mm long. Stamen color is RHSCC White group 155C. Anther color RHSCC Greyed-yellow 162A.

Style: Is 9 mm long. Style number is five per flower. Style color is RHSCC Yellow-green group 148C.

Sepals: Sepal color is RHSCC Yellow-green group 148D, tinged basally RHSCC 187B (Greyed purple). Sepal length 8 mm, and sepal width 4 mm.

Fruit: Fruit examined at harvest time:

Soluble solids: Average 15.7° Brix, with a range of 13.1-17.4° Brix.

Acidity: 0.82% malic acid as determined by titration.

Juice pH: Average 3.5 (range 3.3-3.7).

Firmness: Average 18.7 pounds pressure (range 15.7-21.8 pounds) as measured with a penetrometer.

Shape: Mostly conic.

Starch-iodine index ratings near maturity: Average 5.1 (range 3.6-6.6).

Weight: Average 161 grams (range 94-209 grams).

Fruit diameter: Average 7.0 cm (range 5.5-7.7 cm).

Height: Average 6.5 cm (range 6.0-6.8 cm).

Color: Darkest fruit skin over-color is RHSCC 179A (Greyed-red); lighter fruit skin color is RHSCC N34C (Orange-red). Fruit background color is RHSCC Greyed yellow group 162B. Fruit lenticels are mostly round, prominent, RHSCC (Greyed-yellow) group 161A in color. There is an average of 4.8 fruit skin lenticels per square centimeter.

Stem cavity: Acute, with a depth of 20.3 mm and a width of 28.0 mm. Stem cavity russet color is RHSCC 199C (Grey-brown). Fine smooth russeting of stem cavity russet often extends to the shoulders.

Stem: Very long (31.6 mm) and thin (1.9 mm). Fruit stem color RHSCC 152D (Yellow-green) and N199C (Grey-brown), tinged with 175B (Greyed-orange).

Basin: Abrupt, medium to deep, medium breadth, crowned. Average basin depth 12.6 mm, average basin width 25.1 mm.

Calyx: Persistent and closed, with slightly recurved lobes united at base.

Calyx tube: Urn-shaped.

Stamen remnants: Basal.

Carpels: Roundish, axile and mucronate.

Core position: Median and closed.

Core lines: Meeting, length 26 mm and width 31 mm.

Seeds: Five locules per fruit. Average 8.6 seeds per fruit. Seed length 7.6 mm; seed width 4.4 mm; seed depth 2.9 mm. Acute, pointed, and slightly tufted. Fresh seed color RHSCC Brown group 200B. Dried seed color RHSCC Grey-brown group N199B.

Skin thickness: Medium thick, 0.28 mm.

Flesh: Fruit flesh color is RHSCC White group 155B.

Russet: Covering on average 15% of skin (range 0-30%), RHSCC Grey-brown group 199C.

Texture: Very firm.

Flavor: High sugar and acidity, full flavor and aromatic.

Harvest time: Maturity ranges between October 4 and October 15 in Geneva, N.Y.

Use: Fresh, baking, hard and sweet cider, multiple use.

Keeping quality: Excellent keeping quality with minimal or no disorders after 150 days.

General culture: Apple tree variety 'NY109' is considered as susceptible as other apple varieties to all insects, diseases, and climate-related disorders found in apple production regions of New York. 'NY109' fruit held in cold storage after harvest are susceptible to certain storage disorders, but their occurrence is low, variable, and influenced by the year. Keeping quality in regular cold storage is up to 150 days.

Production & management: 'NY109' can be grown on various rootstocks in both free standing and trellised systems. 'NY109' can be pruned and managed similar to other commercially available apple varieties. Trees require standard management for optimum tree growth and fruit quality. Trees require dormant pruning, fertilization, fruit thinning, and pest control. Crop load management by thinning is especially important.

What is claimed:

1. A new and distinct variety of apple tree named 'NY109' as herein described and illustrated.

* * * * *